United States Patent [19]

McShane et al.

[11] Patent Number: 5,685,811

[45] Date of Patent: Nov. 11, 1997

[54] UNIVERSAL MUSCULAR CONDITIONING DEVICE

[76] Inventors: Jerry M. McShane, 2313 Killarney La., Deer Park, Tex. 77536; Mrugesh M. Shah, 4301 Vista Rd., Pasadena, Tex. 77504; David W. Spinks, 6842 Cedar Lawn Cir., Pasadena, Tex. 77505

[21] Appl. No.: 574,898

[22] Filed: Dec. 19, 1995

[51] Int. Cl.$^6$ .................................................. A63B 21/012
[52] U.S. Cl. ........................... 482/114; 482/115; 482/139
[58] Field of Search ........................... 482/51, 139, 114, 482/115, 118, 124, 127, 128, 908; 602/16, 20, 26, 62, 63; 601/23, 33–35

[56] References Cited

U.S. PATENT DOCUMENTS

| | | | |
|---|---|---|---|
| 4,064,874 | 12/1977 | Valin . | |
| 4,572,170 | 2/1986 | Cronk et al. . | |
| 4,623,141 | 11/1986 | Salvino | 482/127 |
| 4,718,665 | 1/1988 | Airy et al. | 602/16 |
| 4,870,956 | 10/1989 | Fatool et al. . | |
| 5,013,037 | 5/1991 | Stermer | 602/16 |
| 5,036,837 | 8/1991 | Mitchell et al. | 602/16 |
| 5,085,210 | 2/1992 | Smith, III . | |
| 5,209,716 | 5/1993 | Frydman et al. | 482/124 |
| 5,244,455 | 9/1993 | Swicegood et al. . | |
| 5,261,871 | 11/1993 | Greenfield . | |
| 5,316,546 | 5/1994 | Lindh et al. | 602/16 |
| 5,382,223 | 1/1995 | Springs . | |
| 5,419,754 | 5/1995 | Hutchins . | |
| 5,573,487 | 11/1996 | Wallner | 482/124 |

FOREIGN PATENT DOCUMENTS 1253188  12/1960  France .................................. 482/118

*Primary Examiner*—Richard J. Apley
*Assistant Examiner*—Jeanne M. Clark
*Attorney, Agent, or Firm*—Richard C. Litman

[57] ABSTRACT

Universal muscular conditioning devices provide for the placement of two bidirectionally acting, frictionally resistant elements on opposite sides of a joint, in order to require a wearer of the device(s) to provide additional muscular exertion against the frictional resistance and thereby build muscular and joint strength. One embodiment includes a wrap which may be adjustably secured about the joint(s) or limb(s) of differently sized persons, thus eliminating the need for numerous such devices to fit different users. The wrap includes a plurality of pockets or sleeves, into which two of the frictionally resistive elements may be placed opposite one another, to the lateral and medial sides of the joint and essentially coaxial with the joint center. The present disclosure provides for different resistive elements, using (1) a variably compressible resilient member which bears against the interiors of the joints of the rotating arms to create friction therein, (2) a geared device in which the gear sectors are formed of a resilient material and are adjustably compressed together to vary the friction therebetween, and (3) a friction disc which is adjustably compressed between the arms. A unitary glove embodiment is also disclosed, with the resistive elements at each joint being formed of unitary lengths of material each having a low yield point, but high fatigue resistance to allow the joints to be flexed and extended innumerable times against the bending resistance of the elements, without damaging them.

6 Claims, 3 Drawing Sheets

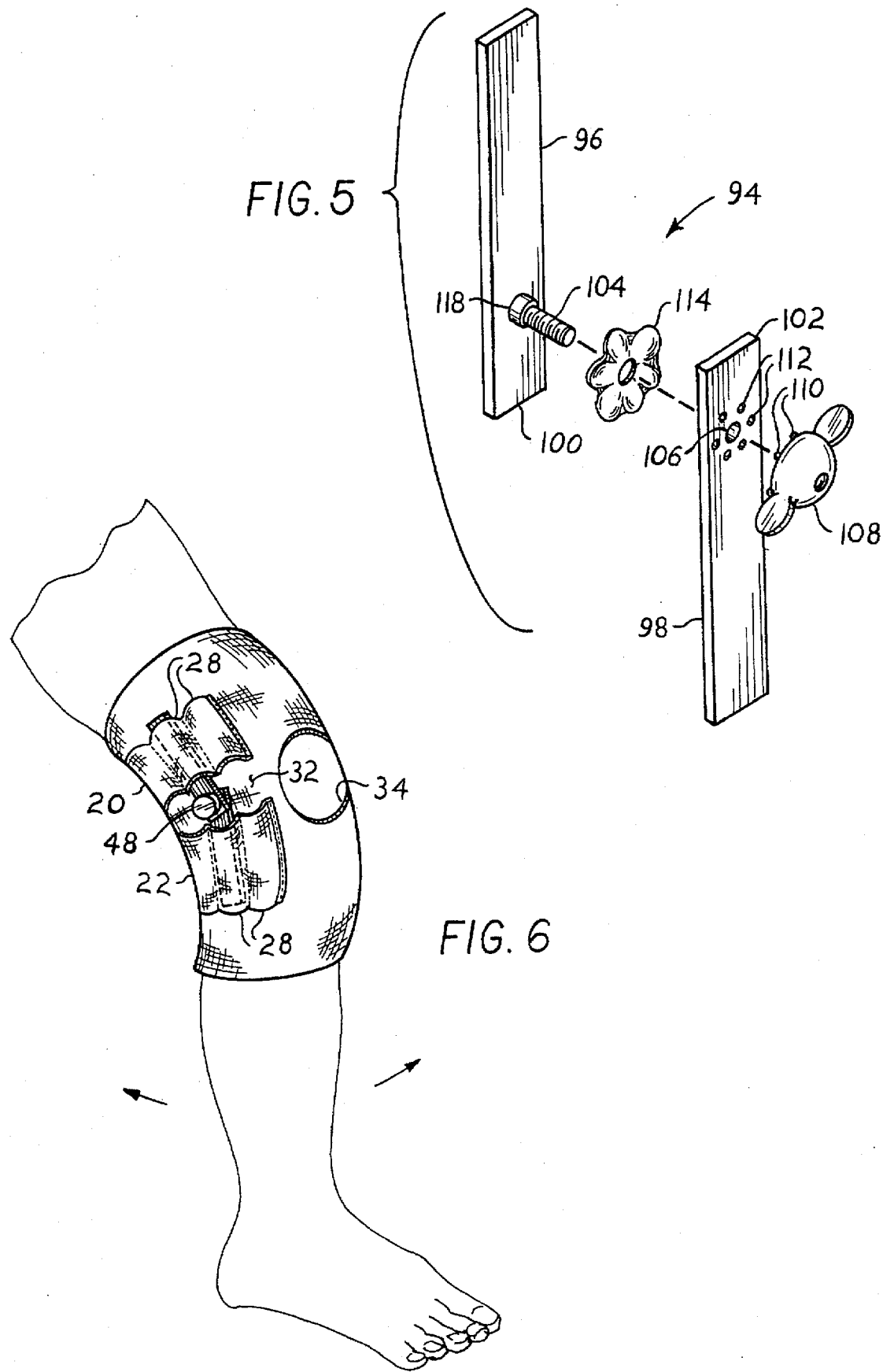

UNIVERSAL MUSCULAR CONDITIONING DEVICE

FIELD OF THE INVENTION

The present invention relates generally to exercise and physical therapy appliances, and more specifically to embodiments of a portable, bidirectional device which is applied to the user to develop increased muscular strength. The various devices may be applied to various joints of the body, and provide a constant resistive force, thereby causing the user to exert additional muscular force to overcome the resistive force, and thereby develop the affected muscle group. The devices may also include predetermined limits to preclude excessive resistance and possible injury to the user.

BACKGROUND OF THE INVENTION

Various braces and supporting devices have been developed in the past for the purpose of supporting a joint during the rehabilitation process after an injury. Such devices generally provide as little friction as possible at the rotary or arcuate hinge mechanism, in order to allow the user to build muscle strength gradually at the joint by using the weight and resistance of his/her own limb as a resistive force against which the strength of the muscles must be applied. However, once the affected joint has been returned to normal or near normal strength, such a brace or support does nothing to provide any further increase in muscular strength, as may be desired by an athlete or other person wishing additional muscular strength.

In order to develop additional strength in a joint, some means of causing the muscle group at the affected joint to produce additional work over and above that normally required, is desired. While various calisthenic exercises, as well as physical sports and games, may be used for this purpose, such sports exercise any given muscle group only irregularly and somewhat randomly, while with calisthenics the various muscle groups are working only against the mass and inertia of the body. Also, in most cases, such exercises are developing any given muscle group only in one direction (e.g., in kicking a ball, lifting a limb against gravity, etc.), rather than applying bidirectional resistive force.

Accordingly, numerous exercise machines have been developed, which operate using hydraulic, pneumatic, electrical, and/or mechanical resistance principles. While many such devices are capable of providing a constant resistive force and/or bidirectional force to a given muscle group or groups, none are portable and are capable of being used while being worn by the user while the user exercises or engages in normal or other activities.

Accordingly, a need will be seen for a universal muscular conditioning device which is portable and which may be applied to any one of a number of orthopedic joints of a user of the device. The device must provide an essentially constant frictionally resistive force at the joint for a user of the device to overcome, and should be bidirectional in nature, providing a resistive force in both directions. Adjustment means should also be provided, as well as means limiting the maximum resistance which may be achieved in order to preclude possible overexertion by a user. While the device is adapted primarily to the development of healthy muscle groups, it may also be used for rehabilitation purposes if desired.

DESCRIPTION OF THE PRIOR ART

U. S. Pat. No. 4,064,874 issued to Norman A. Valin on Dec. 27, 1977 describes a Protective Orthopedic Device comprising a tubular elastic appliance which is secured about the affected joint. The appliance is not adjustable, except by means of any resilience of the elastic. The present device provides adjustable fastening means to fit different joint sizes or circumferences, and thus may be adjusted to fit comfortably on different persons. The Valin device may be too tight on larger persons, while being relatively loose and ineffective on smaller persons. The Valin appliance discloses two sleeves on the inner and outer (medial and lateral) sides of the joint, which sleeves are continuous and provide no access to the hinge point(s) of the brace elements inserted therein. The purpose of the plural sleeves on each side of the joint is to hold two elements on each side of the joint, whereas the multiple, discontinuous sleeves of the present wrap ensure that at least one pair of oppositely disposed sleeves will always be essentially coplanar with the joint axis, no matter what the size of the joint. Valin provides a multiply hinged brace which is of low friction (col. 2, lines 62–64) and provides essentially no resistance to flexion or extension of the joint. The secondary member is formed of spring steel, which by its nature provides an ever changing resistance in one direction according to the spring constant, and a compensating assist in the opposite direction until returning to the neutral point. No adjustment of the force is provided by such a spring steel member; the member must be exchanged for another of a different size, if any change in the force of the member is desired. The present members provide for adjustment of the force, in some embodiments.

U.S. Pat. No. 4,572,170 issued to Richard V. Cronk et al. on Feb. 25, 1986 describes a Preventive Knee Brace including a pair of lateral members hingedly joined on a single plate secured to only the outer or lateral side of the knee by a pair of circumferential straps. The two separate attachment points for the brace members allow the pivot point of each member to rotate independently of the other, unlike the present invention in any of its embodiments. The hinge points are low friction to provide the least possible resistance to movement (col. 5, lines 52–63), unlike the relatively high resistance provided by the present conditioning device. Moreover, the present device includes a wrap type appliance which adjustably secures completely about the joint, unlike the strap arrangement of Cronk et al.

U. S. Pat. No. 4,870,956 issued to Wade Fatool et al. on Oct. 3, 1989 describes a Knee Brace comprising an elastic tubular sleeve of neoprene, with three contiguous pockets formed thereon. The central pocket is larger than the left and right hand pockets. Each of the pockets is adapted to hold a varying number of pneumatic tubes therein, with the tubes being formed in a normally straight configuration and thus resisting flexion of the joint, but assisting in extension (col. 3, lines 44–45), unlike the bidirectional resistance provided by the present appliance in its various embodiments. The larger central pocket is adapted to be placed directly over the patella, unlike the present wrap, which includes a relief hole directly over the knee to preclude binding and to allow for the natural stretch of the skin over the front of the knee. The adjacent side pockets cannot position the elongate members directly at the sides of the knee for all joint sizes, as provided by the present invention with its spaced plural sleeves.

U.S. Pat. No. 5,085,210 issued to Kirby Smith, III on Feb. 4, 1992 describes a Sleeve For Maintaining Position Of Orthopedic Knee Brace, comprising an elastic neoprene sleeve which is positively secured about the calf (not the knee) of a wearer by means of circumferential Velcro (tm) straps. The device cannot be opened to provide for adjustment for different limb diameters of different wearers, as in the present device. The sleeve provides for the holding of only a single brace of conventional design; Smith, III is silent as to the friction developed by the hinge mechanism of such a brace, and/or any bidirectional nature or adjustability of such friction, if any. No means is disclosed for securing the opposite, upper end of the brace; a separate sleeve or wrap of some sort (not disclosed by Smith, III) would be required.

U.S. Pat. No. 5,244,455 issued to George D. Swicegood et al. on Sep. 14, 1993 describes a Knee Hinge adapted for use as a knee brace, with circumferential straps provided to secure the upper and lower arms about the leg of the wearer, to each side of the knee. Two hinged braces are provided, to the medial (inner) and lateral (outer) sides of the knee. Velcro (tm) is used to secure the straps adjustably about the leg of the wearer. The hinge includes a cam fixed to one arm of the device, with a generally cardioid shaped cam follower cutout formed in the other arm. The configuration provides a polycentric hinge mechanism, but Swicegood et al. are silent as to the friction (if to any appreciable degree) which is developed by their mechanism. No means of adjusting any friction of the joint is provided, and it appears that any friction developed would vary depending upon the orientation of the joint and centroid of the configuration, unlike the relatively constant friction developed by the present device.

U.S. Pat. No. 5,261,871 issued to Raphael L. Greenfield on Nov. 16, 1993 describes an Orthopedic Device, which in its embodiment directed to use about the knee, comprises an elastic tubular appliance which is stretched to fit about the leg and knee. No side opening or adjustment is provided. A plurality of relatively small, continuous pockets are provided along each side of the knee brace, adapted for the insertion of varying numbers of spring wires therein. The wires are a nickel-titanium alloy ((col. 7, lines 29–32) in order to provide resistance to bending and yet also provide a very high yield limit in order to avoid permanent deformation. In fact, Greenfield provides for coils to be formed in the wires, to distribute the bending load over a greater length of material in order to avoid exceeding the yield limit and resulting permanent deformation. Accordingly, the Greenfield device resists only flexion of the joint, with the resiliency of the wire assisting the joint in extension. In contrast, the present invention in its embodiment utilizing monolithic bending members, uses soft metal members with a very low yield point but with a high fatigue limit; such metals are commonly used in pronged fasteners adapted to be bent and straightened numerous times, for securing punched papers in file folders and the like. Thus, the movement of a joint having an appliance with such yieldable members secured thereto, results in some resistance to flexion as the members are forced to bend to a new state, and equal resistive force in the opposite direction when the joint is extended as the yieldable metal members are returned to near their original configuration. Other materials (plastics, etc.) having a similar property of low yield strength and high resistance to fatigue, may also be used in the present invention if desired.

U.S. Pat. No. 5,382,223 issued to Michael A. Springs on Jan. 17, 1995 describes a Contoured Orthopaedic Support Having Reduced Skin Irritation Properties. The device is formed of a sheet of fabric covered neoprene material with a single seam, and has no additional bracing means or other components therein. The resilient and elastic neoprene material tends to return to its original extended configuration, thus resisting flexion of a joint but assisting extension of the joint. Such unidirectional action does nothing to work the complementary muscle groups of a joint, which function is served by the present invention and its bidirectional effect in each of its embodiments.

Finally, U.S. Pat. No. 5,419,754 issued to Stephen Hutchins on May 30, 1995 describes a Knee Brace comprising two arms having cooperating gear sectors thereon. The upper gear sector (formed of a plurality of metal pins in an arcuate array between two plates) is smaller than the lower gear sector to provide a differential action, unlike the unitary ratio of the present geared embodiment. The primary distinctions between the Hutchins device and the geared embodiment of the present invention, are that (1) the friction of the Hutchins device is not adjustable, as in the present invention, and (2) Hutchins seeks to minimize friction by forming the gear sectors from a hard material (plastics or metal). The present invention utilizes gear sectors formed of a somewhat resilient material, which is caused to deform when the sectors are adjustably compressed together, thereby changing the friction between the sectors and the bidirectional resistance of the assembly.

None of the above noted patents, taken either singly or in combination, are seen to disclose the specific arrangement of concepts disclosed by the present invention.

SUMMARY OF THE INVENTION

By the present invention, improved universal muscular conditioning devices are disclosed.

Accordingly, one of the objects of the present invention is to provide muscular conditioning devices in various embodiments, each of which provides a predetermined, adjustable, bidirectional resistance to both flexion and extension of a joint to which one of the devices is applied.

Another of the objects of the present invention is to provide improved muscular conditioning devices which provide for universal fit to various joints of persons of different sizes, and which further provide a plurality of pockets or sleeves for the resistance elements to be placed selectively substantially coaxially with the joint to which the device is applied.

Yet another of the objects of the present invention is to provide improved muscular conditioning devices which include limit means to preclude excessive resistance being developed by the device, thereby reducing the potential hazard of overexertion by a user of any of the devices.

Still another of the objects of the present invention is to provide an improved muscular conditioning device, at least one embodiment of which utilizes an adjustably compressible resilient elastomer element which frictionally bears against rotationally mating components, to provide the desired bidirectional resistance.

A further object of the present invention is to provide an improved muscular conditioning device, at least one embodiment of which utilizes mating gear sectors of compressible and resilient material which may be adjustably bound together to adjust the rotational resistance therebetween.

An additional object of the present invention is to provide an improved muscular conditioning device, at least one embodiment of which utilizes an axial pivot upon which a threaded member may be adjustably secured to adjust the compressive force and resulting friction between the rotationally mating components.

Another object of the present invention is to provide an improved muscular conditioning device, at least one embodiment of which comprises a glove including a plurality of unitary, bidirectionally resistive elements disposed therein, which elements may be exchanged to adjust the bidirectional resistance of the device.

A final object of the present invention is to provide improved universal muscular conditioning devices for the purposes described which are inexpensive, dependable and fully effective in accomplishing their intended purpose.

With these and other objects in view which will more readily appear as the nature of the invention is better understood, the invention consists in the novel combination and arrangement of parts hereinafter more fully described, illustrated and claimed with reference being made to the attached drawings.

BRIEF DESCRIPTION OF THE DRAWINGS

FIG. 5 is an exploded perspective view of yet another type of bidirectionally resistive element, showing the means provided to adjustably secure the two arms together and the friction washer means therebetween.

FIG. 6 is a perspective view of the joint wrap of FIG. 1 removably secured about one knee of a user of the present invention, and showing the selective placement of a resistance element within one of the plurality of sleeves thereon.

Similar reference characters denote corresponding features consistently throughout the several figures of the attached drawings.

DETAILED DESCRIPTION OF THE PREFERRED EMBODIMENTS

Figure 1:
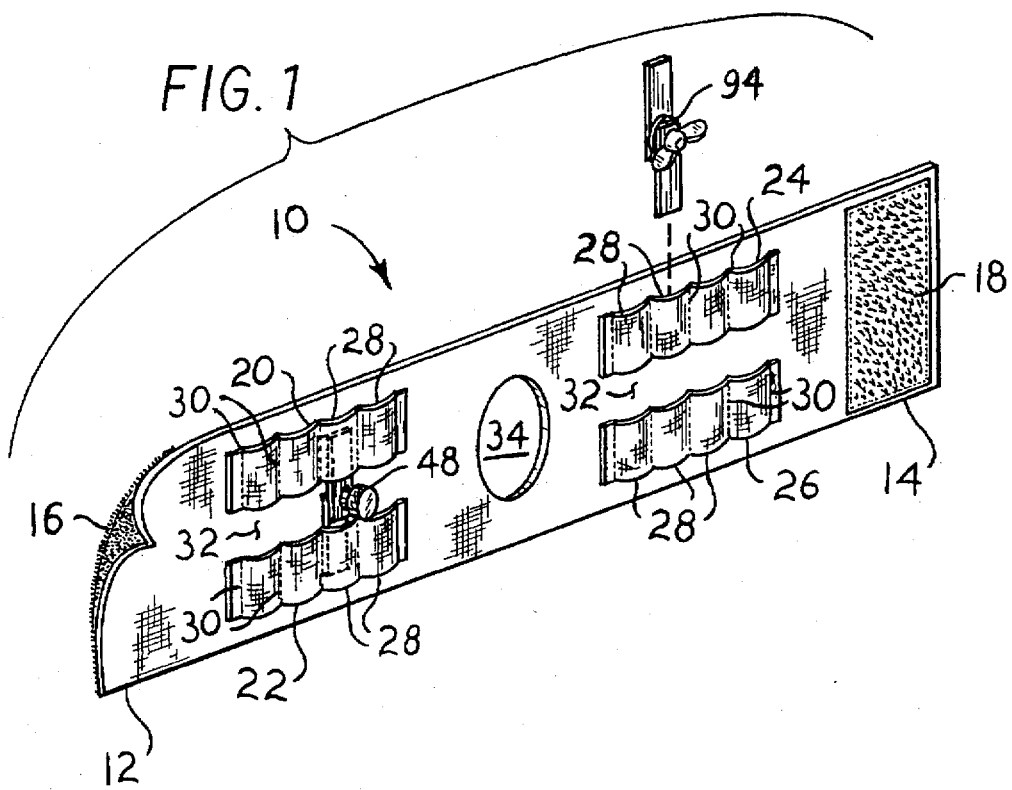
FIG. 1 is a perspective view of an adjustable joint wrap appliance of the present invention, showing the removable installation and selective placement of two different types of bidirectionally resistive elements therein.

Referring now to the drawings, the present invention will be seen to relate to various embodiments of a universal muscular conditioning device, providing for the conditioning and strengthening of muscle groups of various orthopedic joints of the body. The present conditioning device embodiments all operate using the common principle of a flexible wrap or cover which includes removable elongate, bendably resistant elements installable therein and coplanar with the given joint.

FIG. 1 provides a perspective view of an orthopedic joint wrap 10, formed of a relatively thin and flexible material (fabric, etc.). The wrap 10 includes opposite ends 12 and 14, which ends are provided with some means of adjustable closure (e.g., mating hook and loop fastener panels 16 and 18; other means may be used) so the wrap 10 may be secured completely about a limb joint (e.g., knee, elbow, wrist) of a user of the device. The two mating fastener panels 16/18 are preferably relatively wide, in order that the wrap 10 may accommodate a variety of differently sized users.

The wrap 10 includes a series of sleeves of fabric or other suitable material, which are sewn or otherwise secured to the outer surface of the wrap 10. These sleeves form four groups, which are described according to their position on the wrap 10 and relative to the joint about which the wrap 10 is secured. In orthopedics, the side of a joint (e.g., knee) facing outwardly is known as the lateral side, while the opposite, inwardly facing joint is called the medial side, as it is relatively close to the center line of the body in its normal disposition. Accordingly, the present wrap 10 includes an upper lateral sleeve group 20, a lower lateral sleeve group 22, an upper medial sleeve group 24, and a lower medial sleeve group 26. Each of these groups 20 through 26 includes a plurality of individual sleeves 28, with the sleeves 28 of any one group being separated by seams 30 which are sewn through the single sheet of flexible (e.g., fabric) material used to form the sleeves of each group. Each lateral group 20/22 and each medial group 24/26 are aligned immediately above and below one another, with a gap between each upper and lower group 20/24 and 22/26 providing a joint axis opening 32 between each upper and lower sleeve 28 pair.

The wrap 10 is removably secured about an orthopedic joint of a user of the device, as shown in FIG. 6. The central clearance hole 34 is adjusted to be centered over the knee cap, elbow, or other outwardly projecting component of the joint, and the ends 12/14 overlappingly secured about the limb by means of the mating hook and loop fastener material 16/18; the relatively wide expanse of such material ensures that the wrap 10 will secure to itself about limbs of a wide range of circumferences. With the central clearance hole 34 aligned over the knee (as in FIG. 6), elbow, etc., the upper and lower lateral sleeve groups 20 and 22 will be spaced respectively above and below the joint axis of the limb, with a universal fit provided by at least one pair of sleeves 28 of the respective groups 20/22 and 24/26 being positioned substantially in coplanar alignment with the joint axis, depending upon the circumference of the limb. The joint axis opening 32 between the upper and lower groups 20/22 and 24/26 will also be positioned substantially coplanar with the joint axis, by positioning the central clearance opening 34 over the joint. Thus, the portion of the gap or opening 32 between the aligned sleeves 28, will be positioned substantially coaxially with the joint axis.

At this point, two elongate bidirectionally acting frictionally resistant elements (discussed in detail further below) are removably placed within the joint axis aligned sleeves 28, as shown in FIG. 1. (While only one such element is shown installed in the joint axis aligned sleeves 28 of the upper and lower lateral sleeve groups 20 and 22 in the perspective view of FIG. 6, it will be understood that a second element is oppositely installed in the joint axis aligned sleeves 28 of the upper and lower medial sleeve groups 24 and 26.)

The above described wrap 10 and the frictionally resistant elements used therewith, serve to cause the wearer of the device to provide greater exertion for the muscle groups associated with the joint to which the wrap 10 is applied, in order to overcome the frictional resistance of the elements. The muscle groups are exercised in both flexion and extension of the joint, due to the bidirectional nature of the frictionally resistant elements, thus providing a significant advantage over calisthenics and sports, as well as over other bodily attachable devices which use springs or other means to exercise a joint muscle group in only one direction (generally flexion).

However, the above described wrap is most suited for the scale of major joints of the body, such as the elbow and knee. While the frictionally resistant elements used therein could be scaled downward for smaller joints (e.g., fingers, etc.) the cost of the numerous devices required to exercise the fingers of the hand, and their bulk due to the frictional pivot mechanism at each joint, would be impractical. Accordingly, an orthopedic glove 36 may be provided to strengthen the muscle groups associated with the fingers and hand. The glove 36 may be formed of fabric or other flexible material, and is conventional in that it includes the standard finger and thumb digits 38 extending therefrom. However, each of the digits 38 includes two sleeves 40 disposed substantially parallel to the axis of the digit, and opposite one another and substantially coplanar with the joint axis. The sleeves 40 may also be formed of fabric or other flexible material, and may be sewn or otherwise secured to the sides of the digits 38. The distal ends 42 may be closed to better capture therein the bendably resistant elements provided and discussed below.

While other types of resistant elements could be used with the glove 36, unitary, monolithic elongate bidirectionally acting bendably resistant elements 44 and 46 of FIG. 6 have been found to work well, due to their economy and compact size. These elements 44/46 are formed of a material having a relatively low yield strength, but also having extremely high fatigue resistance, thus enabling them to be bent and straightened repeatedly through innumerable cycles without breakage or permanent damage. Various soft metals including lead, solder, and other alloys of lead and tin, enjoy the above required properties, and other materials (plastic, etc.) which have similar properties may also be used.

It may be desirable to vary the bending resistance of the glove digits 38 from time to time, or to vary the resistance between different digits. This may be accomplished with the present invention, by providing bendable resistance elements having different diameters (and thus different cross sectional areas and bending strengths), e.g., the larger diameter first element 44 and the smaller diameter second element 46 of FIG. 6. Other configurations may be used, such as elements having an essentially constant diameter with the exception of a short portion of predetermined diameter and bending resistance, adapted to lie coaxially with the particular joint. In any case, the bidirectionally resistive elements 44/46 of the glove 38 serve to exercise the muscle groups of the appropriate digits of the hand, in both flexion and extension, unlike mere "grip strengthening" devices and exercises, such as hard rubber balls, etc., which serve only to strengthen the flexion of the fingers and compressive grip of the hand, and do nothing to strengthen the fingers and thumb in extension.

Figure 3:
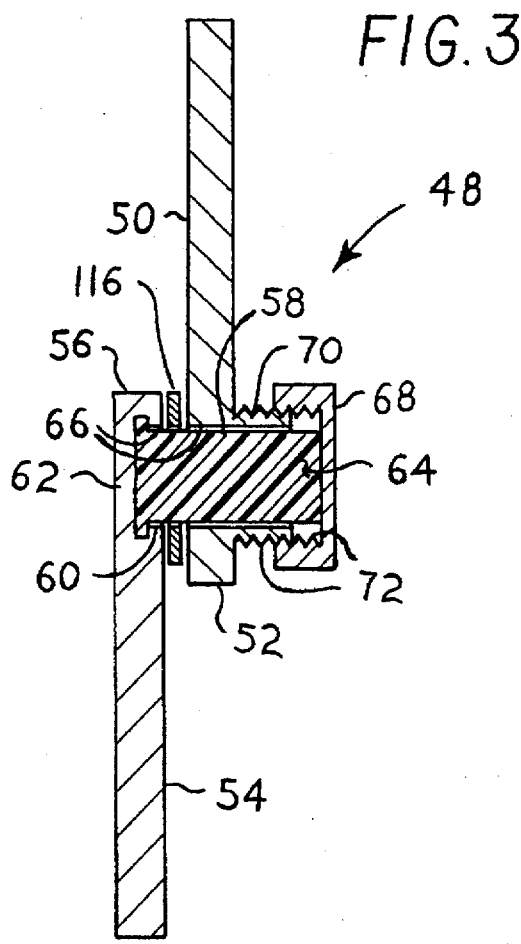
FIG. 3 is a front elevation view in section of one type of bidirectionally resistive element of the present invention, showing the adjustable frictional resistance provided by compressing a resilient elastomer element therein.
Figure 4:
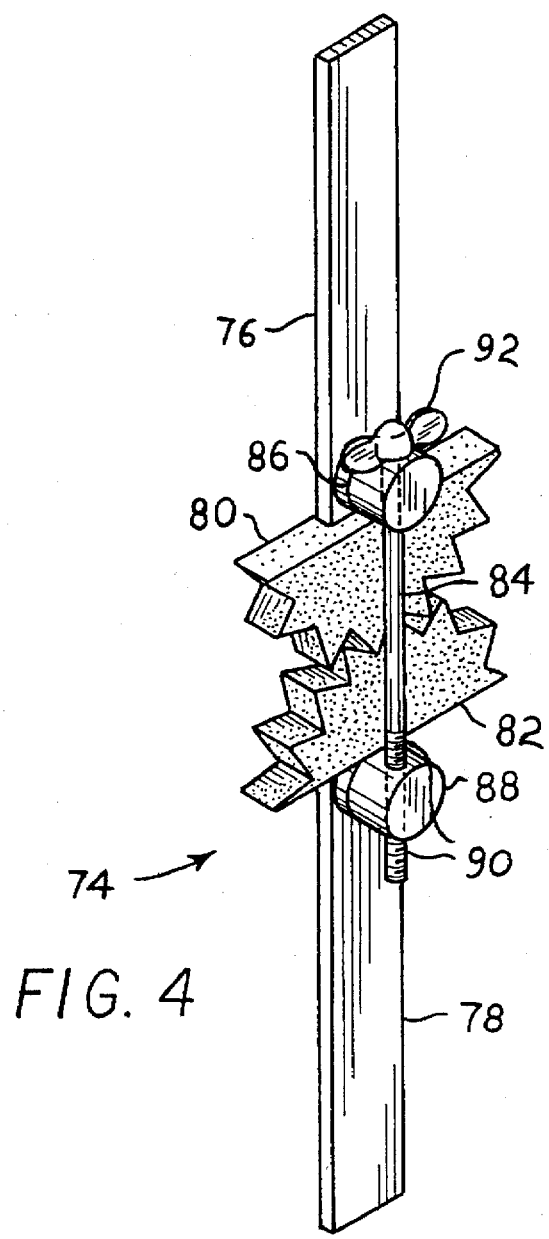
FIG. 4 is a perspective view of another type of bidirectionally resistive element, showing the adjustable compression of mating resilient gear sectors to provide the adjustable resistance.

FIGS. 3 through 5 disclose details of three different mechanisms which may be used to provide the desired bidirectional frictional resistance of such elements as may be used in combination with the wrap 10 of FIGS. 1 and 6. In FIG. 3, an elongate bidirectionally and frictionally resistive element 48 includes a first or upwardly extending arm 50 having a friction joint end 52, and an opposite second or downwardly extending arm 54 having a friction joint end 56. The first arm friction joint end 52 includes a circular hole or passage 58 formed completely therethrough, while the second arm friction joint end 56 includes a "blind" hole 60 (i.e., one which does not completely penetrate the arm 54) with a bottom 62 defined by the outer surface of the friction joint end 56 of the second arm 54. (Alternatively, the hole 60 may be formed completely through the arm 54 if desired, with an outer plate provided thereover to form the hole bottom.)

A resilient, elastomer plug 64 (neoprene, etc.) having a normal diameter closely fitting the interior walls 66 of the passage and hole 58/60, is captured within the walls 66, the hole bottom 62 of the second arm joint end 56, and a cap 68 secured over the first arm friction end passage 58. A sleeve 70 is provided which extends from the friction end passage 58 and which is coaxial therewith. The sleeve 70 and cap 68 may include mating threads 72, thus allowing the cap 68 to be threaded toward or away from the first arm 50, respectively compressing the resilient plug 64 or allowing it to expand. When the plug 64 is compressed axially between the cap 68 and the hole bottom 62, it will expand outwardly as a result, thus binding against the walls 66 of the passage and hole 58/60 to adjust the frictional resistance of the element 48 as desired.

Preferably, some means should be provided to preclude excessive frictional resistance in any of the elements provided with the present invention. This is an important consideration, as such excessive resistance may result in overexertion of the muscle group(s) and possible injury to the user of the device. Thus, the element 48 of FIG. 3 includes a relatively short thread length of predetermined depth, as indicated by the relatively short cap 68 and sleeve 70. (Other means may be used, e g., cutting the threads only partially along the sleeve 70 and/or within the cap 68, etc.) This ensures that even if the cap 68 is secured to its threaded limit on the sleeve 70, the resulting axial compression of the resilient plug 64 and expansion within the walls 66 of the joint members 52/56, will be insufficient to cause excessive frictional binding and overexertion of a user of the device.

FIG. 4 provides a perspective view of an alternative embodiment of an element 74, wherein the upper and lower arms 76/78 each respectively include a first gear sector 80 and matingly engaged second gear sector 82, which sectors 80/82 comprise the friction joint ends of the two arms 76/78. The gear sectors 80/82 are compressed together by an elongate connector 84 extending across the two sectors and securing the two friction joint ends and sectors 80/82 together. Each of the arms respectively includes a first and a second pivot 86/88 thereon, with the connector 84 being placed in tension between the pivots 86/88 to urge the sectors 80/82 compressibly together. By forming the gear sectors 80/82 of a compressible, resilient material (neoprene, etc.), they will be distorted when compressed, thereby providing a frictional resistance to their meshing as the arms 76/78 move arcuately relative to one another.

Adjustment of the compression of the resilient gear sectors 80/82, and thus the frictional resistance of the arcuate movement of the arms 76/78 relative to one another, is achieved by threading one end 90 of the connector 84 and providing mating threads in the respective pivot, e.g., the second pivot 88. A wing screw type element 92, or other easily manipulated component, may be provided at the opposite end of the connector 84 to enable the user to adjust the tension of the connector between the two arms 76/78, and thus the compression of the gear sectors 80/82 and their resulting frictional resistance. The connector threads 90 may be limited in their length, thus providing a limit to the compression, and resulting frictional resistance, which may be applied to the gear sectors 80/82 to preclude overexertion of the user of the device.

FIG. 5 provides an exploded perspective view of yet another alternative means of providing the desired frictional resistance. In FIG. 5, an element 94 includes a first or upper arm 96 and a second or lower arm 98, with the arms 96/98 respectively having friction joint ends 100/102. The first or upper arm 96 includes an attachment stud or shaft 104 extending normal to the joint end 100, with the second or lower arm 98 having a cooperating passage 106 through the friction joint end thereof. The two arms 96/98 are assembled with the attachment shaft 104 passing through the passage 106, and a retainer 108 is secured to the protruding end of the shaft 104 to sandwich the second arm friction joint end 102 between the retainer 108 and the first arm friction joint end 100. The retainer 108 may comprise a wing nut for adjusting the friction of the assembly, with the nut precluded from turning by a plurality of protrusions 110 on the face thereof, which engage a like plurality of depressions 112 on the face of the second arm friction end.

In order to refine the coefficient of friction between the two arms 96 and 98, a spring washer 114 (e.g., Belville washer) may be sandwiched between the two friction joint ends 100/102. As the wing nut 108 is threaded more tightly onto the cooperatingly threaded shaft 104, the spring washer 114 is resiliently compressed, with the alternatingly raised portions on each side bearing more tightly against the adjacent friction face of each respective joint end 100/102. (A standard washer 116 may be provided between the two friction joint ends 52 and 56 of the friction element 48 of FIG. 3, if desired, but serves only to smooth the action between the two joint ends 52 and 56 rather than to provide additional friction, as in the spring washer 114 of the friction element 94 of FIG. 5. The friction of the friction element 48 of FIG. 3 is provided by means of the lateral expansion of the resilient cylinder 64, as described further above.) The nut 108 may be turned manually by overriding the retention means of the protrusions and depressions 110/112, but will remain secure at the predetermined setting once adjusted.

As in the other friction element embodiments, the friction element 94 of FIG. 5 also includes means limiting the maximum friction which may be developed by the device. The threaded stud or shaft 104 may include a limited thread length with a base having a relatively larger diameter unthreaded shoulder portion 118 thereon, past which the nut or retainer 106 cannot be threaded. This unthreaded portion 118 provides a predetermined minimum space for the spring washer 114, thus limiting the compression of the washer 114 and the friction developed in the joint of the element 92.

The above described friction elements 48, 74, and/or 94, in combination with the wrap 10 described above, provide a light weight and portable means of strengthening a given muscle group(s) associated with a specific orthopedic joint (s) of a user of the present appliance. The user of the appliance need only obtain a generally properly sized wrap 10, and adjustably secure it about his/her knee, elbow, etc. joint, as desired and described further above with the wide expanses of hook and loop fastening material at each end of the wrap 10.

The appropriate elongate friction elements 48/74/94 may be adjusted to provide the desired degree of frictional resistance (up to the predetermined maximum limit inherent in the elements), and inserted into the appropriate opposite upper and lower sleeves 28 which are coplanar with the joint axis, with the connected joint end portions of the inserted friction elements 48/74/94 positioned in the joint axis opening 32 between the upper and lower sleeves 28 and coaxial with the joint axis.

(It should be noted that although different types or embodiments of friction elements may be used on opposite sides of a joint in the same wrap and application, preferably two identical elements are used at a given joint. The showing of two different element types, i.e., 48 and 94, in FIG. 1, is exemplary of the use of the wrap 10 with different types of elements, rather than indicating that different types of elements are to be used in any one application.)

At this point, the wearer of the present device need only exercise or engage in normal activities as desired, with the additional effort required to overcome the friction of the frictional elements, serving to increase the muscular strength of the muscle group of the joint to which the device has been applied. As the frictional elements 48/74/94 each provide bidirectional frictional resistance, the complementary muscle groups of the respective joint will be exercised and strengthened, as the limb and joint are moved both in flexion and in extension.

Figure 2:
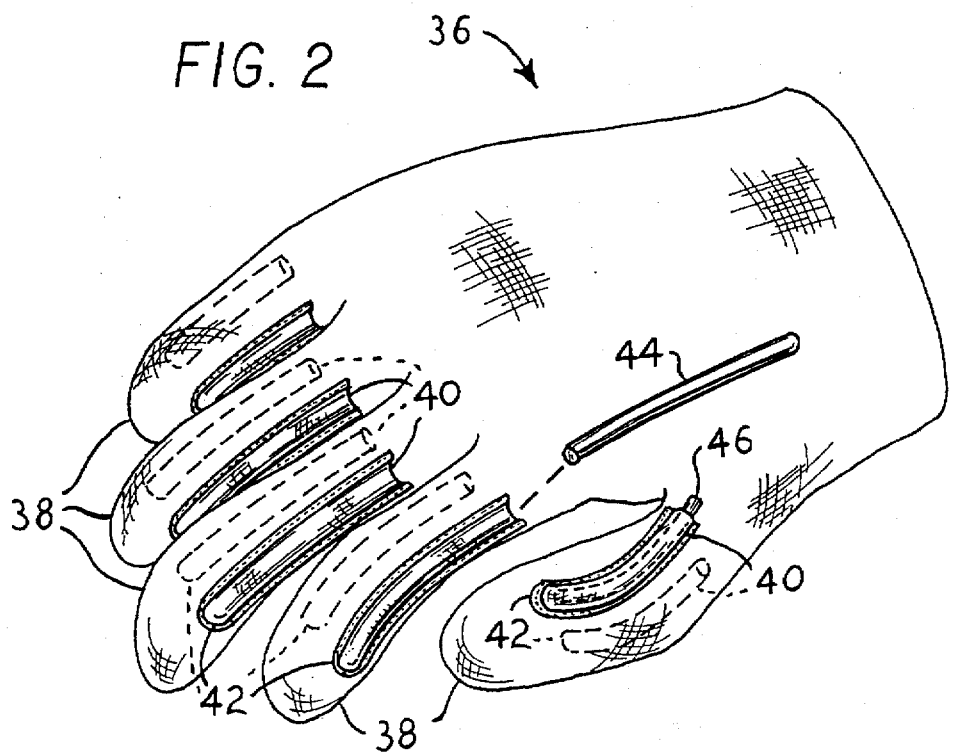
FIG. 2 is a perspective view of a glove embodiment, showing the removable installation of plural unitary bidirectionally resistive elements therein.

On a smaller scale, the glove 36 of FIG. 2 provides an equivalent function for the hand and fingers of a user of the device, with the elongate resistant components 44 and 46 providing the predetermined bending resistance as desired. The elements 44 and 46 are also bidirectionally resistant, thus providing much the same exercise benefits as the larger joint wrap and elements discussed above.

While the above device and its various embodiments will be seen to provide an economical and convenient means for an athlete or other person to strengthen a given muscle group(s), it will also be seen that the present device may also be used in the orthopedic rehabilitation field, under the supervision of qualified medical personnel and with appropriate approvals. The device eliminates the need for costly and complex equipment, and may be used by both ambulatory and non-ambulatory personnel.

It is to be understood that the present invention is not limited to the sole embodiments described above, but encompasses any and all embodiments within the scope of the following claims.

We claim:

1. A universal muscular conditioning device, comprising:

an orthopedic joint wrap comprising an elongate web of flexible material and including a first end and an opposite second end with respective first and second cooperating adjustable closure means disposed thereon, said adjustable closure means providing for the adjustable and removable securing of said wrap about a limb joint of a user of said device;

said wrap further including a plurality of upper lateral sleeves, a plurality of corresponding lower lateral sleeves aligned therewith to form a lateral sleeve group comprising lateral pairs of single upper and lower lateral sleeves having a joint axis opening therebetween, and a plurality of upper medial sleeves, and a plurality of corresponding lower medial sleeves aligned therewith to form a medial sleeve group comprising medial pairs of single upper and lower medial sleeves having a joint axis opening therebetween and;

at least two bidirectionally acting frictionally resistant elements each having a first arm including a first friction joint end having a passage formed completely therethrough, an opposite second arm including a second friction joint end having a blind hole formed partially therethrough, a resilient plug installed through said passage and into said blind hole, wherein said plug substantially fills and binds against said passage and said blind hole, to form a friction joint, providing frictional resistance to rotational movement between said first and second arms, and plug closure means for compressively securing said resilient plug within said passage and said blind hole, each of said frictionally resistant elements being selectively and removably inserted into one of said lateral and medial pairs of sleeves with each said friction joint being positioned within said joint axis opening of said wrap.

2. The muscular conditioning device of claim 1, wherein:
said first and second cooperating adjustable closure means comprises portions of mating first and second hook and loop fastening material.

3. The muscular conditioning device of claim 1, wherein:

said joint wrap is formed of fabric material.

4. The muscular conditioning device of claim 1, wherein:

said upper lateral sleeves, lower lateral sleeves, upper medial sleeves, and lower medial sleeves are each formed of a single sheet of flexible material and each of said sleeves defined and separated by stitching therebetween to secure said sleeves to said wrap.

5. The muscular conditioning device of claim 1, wherein:

said plug closure means comprises an externally threaded sleeve coaxial with said passage and extending from said first friction joint end, and an internally threaded closed cap adjustably and threadedly installed upon said sleeve to provide adjustable frictional resistance for each of said frictionally resistant elements.

6. The muscular conditioning device of claim 5, wherein:

each of said frictionally resistive elements includes stop means precluding the development of excessive frictional resistance therein, comprising a predetermined limited thread length for said sleeve and said cap to preclude compression of said plug past said predetermined thread length.

\* \* \* \* \*